United States Patent [19]  
Ogura et al.

[11] Patent Number: 4,691,012  
[45] Date of Patent: Sep. 1, 1987

[54] SIALIC ACID DERIVATIVE AND PROCESS FOR PREPARING THE SAME

[75] Inventors: Haruo Ogura, Matsudo; Kimio Furuhata, Tokyo; Toshiaki Osawa, Tokyo; Satoshi Toyoshima, Tokyo; Yoshiyasu Shitori, Musashino; Masayoshi Ito, Kunitachi; Shoji Yoshimura, Iruma, all of Japan

[73] Assignee: MECT Corporation, Tokyo, Japan

[21] Appl. No.: 708,638

[22] Filed: Mar. 6, 1985

[30] Foreign Application Priority Data

Mar. 9, 1984 [JP] Japan .................................. 59-44906

[51] Int. Cl.$^4$ ............................................. C07H 17/00
[52] U.S. Cl. ......................................... 536/23; 536/24; 536/55.3
[58] Field of Search ............................. 536/4.1, 23, 24

[56] References Cited

U.S. PATENT DOCUMENTS 3,501,456 3/1970 Shen et al. ........................... 536/4.1
4,447,600 5/1984 Ogura et al. .......................... 536/24

Primary Examiner—Johnnie R. Brown  
Assistant Examiner—John W. Rollins, Jr.  
Attorney, Agent, or Firm—Oblon, Fisher, Spivak, McClelland & Maier

[57] ABSTRACT

A novel N-acetylneuraminic acid derivative, represented by the general formula:

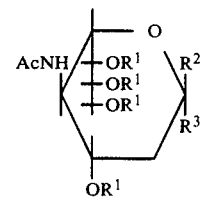

wherein the $R^1$ groups are, independently, hydrogen or acetyl; $R^2$ is a nucleoside residue; and $R^3$ is carboxyl or methoxycarbonyl.

The N-acetylneuraminic acid derivative is useful in inhibiting metastasis of cancer cells. Also provided is a process for the preparation of the derivatives.

16 Claims, No Drawings

SIALIC ACID DERIVATIVE AND PROCESS FOR PREPARING THE SAME

BACKGROUND OF THE INVENTION

The present invention relates to a novel N-acetylneuraminic acid derivative and a process for the preparation thereof. More particularly, it relates to a novel N-acetylneuraminic acid derivative which has utility as a medicine which remarkedly inhibits the metastasis of cancer cells, and a process for preparing the same.

It has been known in the art that N-acetylneuraminic acid, which is referred to as sialic acid, occupies the glycoside terminals of a composite glycoside, such as glycolipid and glycoprotein, present at cell surfaces to provide important effects on the differentiation, maturity, functions and intercellular actions of organic cells. A variety of N-acetylneuraminic acid derivatives has been synthesized and subjected to research work.

Such prior art references are, for example, as follows:

R. Kuhn, P. Lutz und D. L. MacDonald, Chem Ber., 99 611–617 (1966), Synthese anomerer Sialinsäuremethylketoside.

P. Meindl und H. Tuppy, Mh. Chem., 100 1295–1306 (1969), Über 2-Deoxy-2,3-dehydro-sialinsäuren, I. Mitt.: Synthese und Eigenschaften von 2-Deoxy-2,3-dehydro-N-acylneuraminsäuren und deren Methylestern.

R. Brossmer, H. Friebolin, G. Keilich, B. Löser and M. Supp, Hopp-Seyler's Z. physiol. Chem., 359 1064 (1978) Synthesis of Disaccharides Containing N-Acetyl-D-neuraminic Acid.

M. N. Sharma and R. Eby, Carbohydr. Res., 127 201–210 (1984), Synthesis and Conformational Studies of 2-β-Chloro,2-α.Fluoro, and 2-β-Fluoro-Derivatives of 2-Deoxy-N-acetylneuraminic acid.

L. Holmquist and R. Brossmer, Hoppe-Seyler's Z. Physiol, Chem., 353 1346–1350 (1972), Synthesis and Properties of the 2-Aminoethyl α- and the 2-Pyridyl α- and β-Ketosides of N-Acetyl-D-neuraminic Acid.

L. Holmquist and R. Brossmer, FEBS Letters, 22 46–48 (1972), ON THE SPECIFICITY OF NEURAMINIDASE: The carboxymethyl α-ketoside of N-acetyl-D-neuraminic acid, a Vibrio cholerae neuraminidase substrate having two anionic sites.

T. Ogawa and M. Sugimoto, Carbohydr. Res., 128 C1–C4 (1984), Synthesis of α- and β-(2-9)-linked disialylglycerolipids.

H. Paulsen and H. Tietz, Carbohydr. Res., 125 47–64 (1984), Synthese eines trisaccharides aus N-acetylneuraminsäure and N-acetyllactosamin.

We have previously found that the N-acetylneuraminic acid derivative having a nucleoside or glucose coupled to the N-acetylneuraminic acid through α-bonding has excellent physiological activities, and have already filed a patent application relating to such a derivative and the process for preparing the same based on that finding (Japanese patent application No. 77672/1981; corresponding U.S. patent application which has matured to United Pat. No. 4,447,600).

We have now found that a novel N-acetylneuraminic acid derivative, in addition to the previously found derivative, in which the nucleoside is coupled through β-bonding to the N-acetylneuraminic acid can be isolated and purified by applying unique dual-chromatography in the aforementioned known process. Furthermore, we were surprised to find that the novel derivative isolated and purified as aforementioned has a pronounced and unique pharmaceutical efficacy as regards inhibition of metastatis of cancer cells. The present invention has been accomplished on the basis of this finding.

SUMMARY OF THE INVENTION

The N-acetylneuraminic acid derivative provided in accordance with the invention is represented by the following general formula:

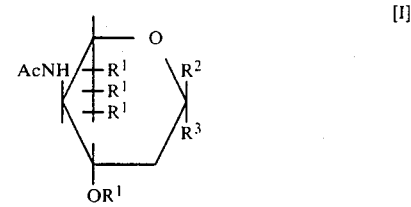

wherein $R^1$ are, independently, hydrogen or acetyl; $R^2$ is a nucleoside residue; and $R^3$ is carboxyl or methoxycarbonyl.

Also provided, according to the invention, is a process for preparing the N-acetylneuraminic acid derivative represented by the general formula [I] set forth above, the process comprising the reaction step of reacting a compound represented by the general formula:

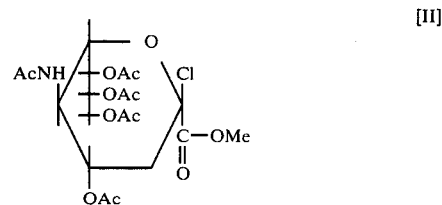

with a compound represented by the formula $R^2$-H [III], wherein $R^2$ is a nucleoside residue, in the presence of a catalyst; and the step of isolating and purifying the reaction product of the preceding step through dual-chromatography subsequent to an optional step of hydrolyzing the reaction product.

DETAILED DESCRIPTION OF THE INVENTION

As has been described hereinbefore, the present invention relates to novel N-acetylneuraminic acid derivatives and a process for preparing the same.

The N-acetylneuraminic acid derivatives which have not been known previously and found by the inventors as novel compounds are represented by the following general formula [I]:

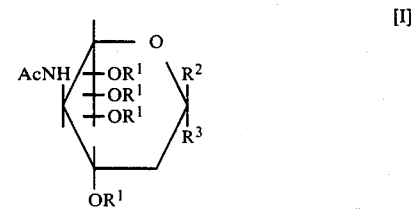

wherein $R^1$ are, independently, hydrogen or acetyl; $R^2$ is a nucleoside residue; and $R^3$ is carboxyl or methoxycarbonyl.

Meanwhile, the term "nucleoside residue" as used throughout the specification and claims means ribose coupled with a purine or a pyrimidine base through a glycoside bond. Ribose or respective bases in the "nucleoside residues" as defined above, may have a substituting group and/or may include a condensation ring. Examples of such nucleoside residue are set forth below.

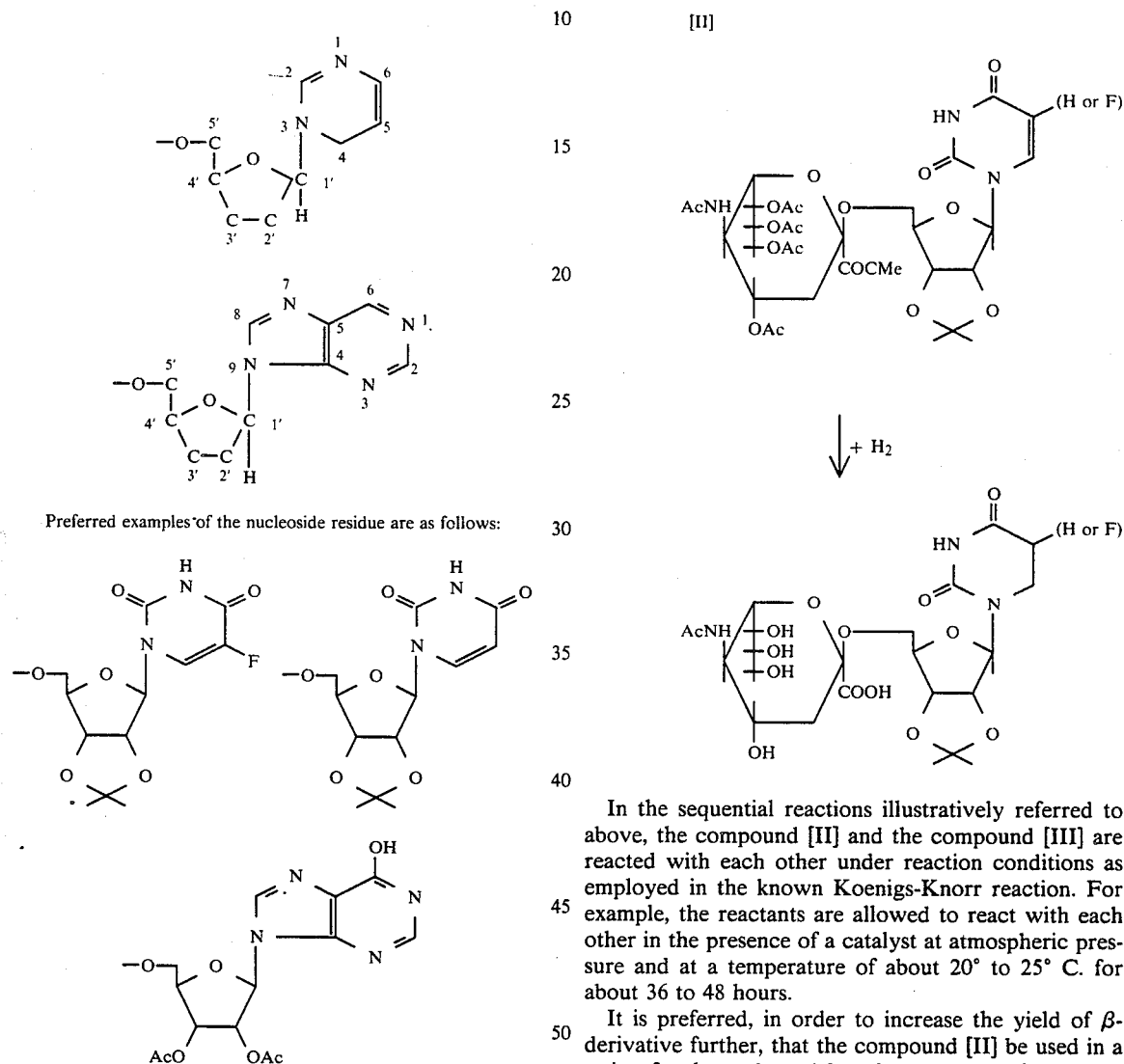

Preferred examples of the nucleoside residue are as follows:

A variety of specific examples of the residue represented by the structural formulae set forth above will become apparent from the Examples referred to hereinafter.

The compounds of the present invention represented by the general formula [I] can be prepared following the procedure illustratively shown, for example, by the following reaction equation, and then isolated and purified through the dual-chromatographic methods which will be described in detail hereinafter. In the following sequential reaction equations, the compound represented by the formula [III] is a known compound and may be conveniently used in the invention in the course of synthesis of various compounds as an intermediate compound.

In the sequential reactions illustratively referred to above, the compound [II] and the compound [III] are reacted with each other under reaction conditions as employed in the known Koenigs-Knorr reaction. For example, the reactants are allowed to react with each other in the presence of a catalyst at atmospheric pressure and at a temperature of about 20° to 25° C. for about 36 to 48 hours.

It is preferred, in order to increase the yield of β-derivative further, that the compound [II] be used in a ratio of at least about 1.2 mols per 1 mol of the compound [III] in the reaction represented by the reaction equation set forth above. For the same purpose, it is also preferable to add fresh changes of the compound [II] and the catalyst at intermediate stages of the reaction step, for instance after about 12 to 24 hours from the initiation of the reaction. It is, of course, necessary that the amounts of the starting materials or compounds and the catalyst used be maintained in the aforementioned reasonable range, when the latter-mentioned intermediate supplementation process is employed.

Amongst the catalysts commonly used in the Koenigs-Knorr reaction, mercury (II) bromide (mercuric bromide), mercury (II) cyanate (mercuric cyanate) or silver perchlorate must be used in the process of the invention. Mercuric bromide and mercuric cyanate are the most preferred to improve the yield and the selectivity. The catalyst is used in an amount ranging from about 1 to 4 equivalents to the compound [II].

Solvents usable in preparation of the compound of the invention include acetonitrile, nitromethane, acetone and methylene chloride. The most preferred solvents are acetone and acetonitrile.

The thus formed reaction product is isolated and purified through dual-chromatography. The term "dual-chromatography" as used throughout the specification and claims means the process in which purification is effected by a combination of two or more adsorption chromatography and/or partition chromatography steps carried out under different conditions. As has been described hereinbefore, although a derivative of N-acetylneuraminic acid having a nucleoside coupled through α-bonding was produced by the process disclosed by our preceding patent application (Japanese patent application No. 77672/1981; corresponding to a United States patent application which has matured to U.S. Pat. No. 4,447,600), no N-acetylneuraminic acid derivative having a nucleoside residue coupled through β-bonding could be obtained. However, according to the present invention, an N-acetylneuraminic acid derivative having a nucleoside residue coupled through β-bonding has been isolated and obtained in the purified state, in addition to the α-derivative, by the utilization or employment of the aforementioned dual-chromatography.

The combinations of different chromatographic processes which may be used as the dual-chromatography in the present invention include, for example, the following:

adsorption chromatography/adsorption chromatography;
adsorption chromatography/partition chromatography;
partition chromatography/adsorption chromatography;
and partition chromatography/partition chromatography.

In consideration of the improvement in isolation, the combination of partition chromatography/adsorption chromatography is the most preferred.

Fillers to be packed in a column for the absorption chromatography and conveniently used in the invention include, for example, silica gel and alumina, silica gel being particularly preferred. On the other hand, developers which may be used in the invention include chloroform, methanol, ethyl acetate, ethanol, benzene, acetone and toluene. Fillers to be packed in a column for the partition chromatography and conveniently used in the invention include, for example, silica gel and alumina, silica gel being preferred. Similar developers as usable in the adsorption chromatography may be also used in the partition chromatography step.

Detailed operations and conditions for the dual-chromatography will become apparent from the descriptions in the Examples given below.

The compounds, according to the present invention, represented by the general formula [I] have noticeable pharmaceutical efficacies to inhibit metastasis of cancer cells.

This function of inhibiting metastatis of cancer cells was ascertained by the test described in the Reference Example which will be given hereinafter.

The present invention will now be described by referring to specific Examples. It should be noted here that the following Examples are set forth by way of example only, and they are not intended to restrict the invention.

EXAMPLE 1

Preparation of 2′,3′-isopropylidene-5′-o-(4-N-acetyl-2,4-dideoxy-3,6,7,8,-tetra-o-acetyl-1-methoxycarbonyl-D-glycero-β-D-galacto-octapyranosyl) uridine:

Into 50 ml of acetonitrile were added 1 gram of 2′,3′-isopropylideneuridine, 300 mg of mercuric cyanate, 600 mg of mercuric bromide and 1 gram of molecular sieve (4A) for suspension in acetonitrile, and the resultant suspension was agitated at room temperature for 30 minutes.

1.5 grams of methyl-2-chloro-4,7,8,9-tetra-o-acetyl-β-D-N-acetylneuraminate (hereinafter referred to as compound [II]) was reacted with the aforementioned suspension, agitated at room temperature for 16 hours, and further added with 510 mg of the compound [II], 150 mg of mercuric cyanate and 300 mg of mercuric bromide, followed by agitation for 24 hours. The reaction mixture was then filtered, and the solvent was distilled off to dryness.

The resultant powder-form substance was dissolved in 100 ml of water and the insoluble materials were removed. The thus obtained solution was treated with ether to remove the substances which were dissolved in ether, and then the residual aqueous solution was saturated with potassium chloride followed by extaction with ethyl acetate. The solution in ethyl acetate was dried with Glauber's salt, filtered, and then the solvent was distilled off to obtain 2.3 grams of a raw product.

2.3 grams of the solid raw product was subjected to column chromatography using an alumina-packed column (Merck, Aluminoxid 90, 70 to 230 meshes ASTM) which was packed by the use of ethyl acetate acetate, and eluted with ethyl, a mixture of ethyl acetate/ethanol (5:1), a mixture of ethyl acetate/ethanol (3:1) and then with ethanol in this order, whereby a mixture of the captioned compound (hereinafter referred to as the β-isomer) and 2′,3′-isopropylidene-5′-o-(4-N-acetyl-2,4-dideoxy-3,6,7,8,-tetra-o-acetyl-1-methoxycarbonyl-D-glycero-α-D-galcto-octapyranosyl) uridine (hereinafter referred to as α-isomer) was eluted.

1.9 grams of the mixture was again eluted through alumina column chromatography (Alumina: 100 g) using a mixture of ethyl acetate and ethanol (6:1) as a solvent, whereby 120 mg of the β-isomer (Yield: 4.5%) and 300 mg of the α-isomer (Yield: 11.2%) were isolated, respectively, in the form of colorless powder. The residual portion was eluted while forming a mixture of the α-isomer and β-isomer.

In isolation through column chromatography, the aforementioned alumina column chromatography was replaced by silica gel column chromatography [Merck, Lober, pre-packed column size B (310-25) Lichroprep Si 60 (40~63 μm)], whereby 830 mg of the β-isomer (Yield: 31.1%) and 210 mg of the α-isomer (yield: 7.9%) could be isolated. In this modified process, chloroform/methanol (60:1) was used as the solvent and was passed through the column at a flow rate of 5 ml/minute.

Physical Properties of the β-isomer $[\alpha]_D^{22} + 3.4°$ (C=1, in methanol).

Ultimate Analysis: $C_{32}H_{43}O_{18}N_3$; Molecular Weight=757.70. Cald.: C; 50.73, H; 5.72, N; 5.55. Found; C; 50.42, H; 5.80, N; 5.36.

Mass Spectrograph m/Z 757(M+), 742(M+ −15), 714(M+ −43), 698(M+ −59).

IR $\nu_{max}^{KBr}$ 1753, 1680 and 1535 cm$^{-1}$.

'H-NMR (CDCl$_3$) δH (TMS). 1.37 (s, 3H), 1.56 (s, 3H), 1.88 (s, 3H), 1.99 (s, 3H), 2.01 (s, 3H), 2.05 (s, 3H), 2.12 (s, 3H), 2.46 (dd, 1H, J=4.8 and 12.9 Hz), 3.82 (s, 3H), 5.72 (d, 1H, J=2.1 Hz), 5.83 (d, 1H, J=8.4 Hz), 7.35 (d, 1H, J=8.4 Hz), 9.83 (broad s, 1H).

EXAMPLE 2

Preparation of 2',3'-isopropylidene-5'-o-(4-N-acetyl-2,4-dideoxyl-1-carboxyl-D-glycero-β-D-galacto-octapyranosyl) uridine 185 mg of the β-isomer obtained in Example 1 was added with 10 ml of a 1N-NaOH, and the resultant solution was agitated at room temperature for 2 hours. Then, the solution was added with 20 ml of water and cooled on ice, and the pH value of the solution was adjusted to pH 3.0 using Dowex-50 (H+), followed by filtration and freeze-dried. The thus obtained powder was dissolved in 20 ml of methanol and treated with activated carbon, filtered, concentrated to have a volume of 5 ml, and added with ethyl acetate to obtain a colorless powder which was dried by phosphorus pentoxide to obtain the captioned compound at a yield of 82%.

Physical Property $[\alpha]_D^{25}$ −12° (C=1, in methanol).

Ultimate Analysis: $C_{23}H_{33}O_{14}N_3$; Cald.: C; 48.00, H; 5.78, N; 7.30. Found: C; 47.91, H; 5.84, N; 7.25.

UV $\lambda_{max}^{MeOH}$nm (log ε); 260 (3.96).

IR $\nu_{max}^{film}$1660, 1530 cm$^{-1}$.

'H-NMR D$_2$O δH (DSS) 1.40 (s, 3H), 1.58 (s, 3H), 1.70 (dd, 1H, J=12.8 and 11.5 Hz), 2.03 (s, 3H), 2.43 (dd, 1H, J=12.8 and 3.8 Hz), 5.82 (broad s, 1H), 5.85 (d, 1H, J=8.1 Hz), 7.72 (d, 1H, J=8.1 Hz).

EXAMPLE 3

Preparation of 5-fluoro-2',3'-isopropylidene-5-o-(4-N-acetyl-2,4-dideoxy-3,6,7,8,-tetra-o-acetyl-1-methoxycarbonyl-D-glycero-β-D-galacto-octapyranosyl) uridine Into 50 ml of acetonitrile were suspended 500 mg of 5-fluoro-2',3'-isopropylideneuridine, 300 mg of cupric cyanate, 600 mg of mercuric bromide and 1 gram of molecular sieve (4A). The suspension was reacted with 1.2 grams of the compound [II] (the same compound as used in Example 1), followed by agitation at room temperature for 16 hours; and then added with an additional 510 mg of the compound [II], 150 mg of mercuric cyanate and 300 mg of mercuric bromide followed by agitation for 24 hours. The reaction liquid was filtered, and the filtrate was subjected to distillation at 40° C. under reduced pressure to remove the solvent, whereby an oily product was left. 100 ml of water was added to the oily product, the insoluble matters being removed, and then treated with ether to remove the substances soluble in ether. Thereafter, the aqueous solution was saturated with potassium chloride, and subjected to extraction with ethyl acetate. The resultant solution in ethyl acetate was dried by the use of Glauber's salt, and the solvent was distilled off to obtain 1.5 grams of another oily product.

The latter-mentioned oily product was subjected to isolation through column chromatography using a silica gel column packed with a silica gel (200 g, Merck, Silica Gel 60, 70 to 230 meshes ASTM) and using CHCl$_3$/methanol (30:1), whereby a mixture of the captioned compound and an isomer thereof were formed. The resultant fraction was concentrated and dried to obtain 580 mg of a raw product.

The raw product was subjected to silica gel column chromatography (Merk, Lobar, size C, Lichroprep Si 60) using CHCl$_3$/methanol (60:1) as an eluent which was passed through the column at a flow rate of 10 ml/minute. The captioned compound was isolated by means of a detector to take up the fraction of UV (290 nm), and then refined to obtain 300 mg of the captioned compound. Yield: 23%. At the same time, 210 mg (Yield: 16%) of an isomer was obtained. This isomer was 5-fluoro-2',3'-isopropylidene-5'-o-(4-N-acetyl-2,4-dideoxy-3,6,7,8,-tetra-o-acetyl-1-methoxycarbonyl-D-glycero-α-D-galactooctapyranosyl) uridine. The yield of pure isomer was 85 mg (Yield: 11%).

Physical Properties of Captioned Compound $[\alpha]_D^{25}$ +11.0° (C=1, in methanol).

Ultimate Analysis: $C_{32}H_{42}O_{18}N_3F$; Cald.: C; 49.55, H; 5.42, N; 5.45. Found: C; 49.34, H; 5.65, N; 5.22.

Mass Spectrograph m/Z 775 (M+), 760 (M+ −15), 732(M+ −43), 716(M+ −59).

IR $\nu_{max}^{KBr}$1735, 1680, 1530 cm$^{-1}$.

'1H-NMR (CDCl$_3$) δH (TMS) 1.37 (s, 3H), 1.56 (s, 3H), 1.87 (s, 3H) 1.99 (s, 6H), 2.02 (s, 3H), 2.13 (s, 3H), 2.50 (dd, 1H, J=14 and 3.5 Hz), 3.77 (s, 3H), 5.54 (broad s, 1H), 7.44 (dd, 1H, J=8 Hz).

EXAMPLE 4

Preparation of 5-fluoro-2',3'-isopropylidene-5'-o-(4-N-acetyl-2,4-dideoxy-1-carboxyl-D-glycero-β-D-galacto-octapyranosyl) Uridine Using the compound as produced in Example 3, the captioned compound was obtained at a yield of 80% following the procedures as described in Example 2.

Physical Properties $[\alpha]_D^{25}$ −9.2° (C=1, in methanol).

Ultimate Analysis: $C_{23}H_{32}O_{14}N_3F$; Cald.: C; 48.08, H; 5.61, N; 7.31. Found: C; 48.05, H; 5.48, N; 7.42.

IR $\nu_{max}^{KBr}$ 3400, 1688, 1580 cm$^{-1}$.

'H-NMR (D$_2$O) δH (DSS) 1.40 (s, 3H), 1.58 (s, 3H), 1.74 (t, 1H, J=14 Hz), 2.04 (s, 3H), 2.48 (dd, 1H, J=14 and 3.5 Hz), 5.86 (broad s, 1H), 7.95 (d, 1H, J=8 Hz).

EXAMPLE 5

Preparation of 2',3'-isopropylidene-5'-o-(4-N-acetyl-2,4-dideoxy-1-methoxycarbonyl-D-glycero-β-D-galacto-octapyranosyl) uridine 500 mg of 2',3'-isopropylidene-5'-o-(4-N-acetyl-2,4-dideoxy-3,6,7,8,-tetra-o-acetyl-1-methoxycarbonyl-D-glycero-β-D-galacto-octapyranosyl) uridine, corresponding to 0.66 millimol, dissolved in 10 ml of methanol was added with 10 ml of a methanol solution containing 100 mg (4.35 millimols) of metallic sodium, while being maintained on an ice bath, and the mixture was agitated for 20 minutes. The mixed solution was neutralized using 1 gram of Dowex 50-X8 (H+), and the neutralized solution was filtered, concentrated, dried until solidified. The solidified mass was dissolved in a small quantity of water, freeze-dried and then dried in vacuo to obtain 350 mg of a colorless and amorphous solid (Yield: 90%). 200 mg of the amorphous solid was subjected to silica gel chromatography and fractionated using chloroform/methanol (10:1) to obtain 150 mg (Yield: 75%) of the captioned compound of amorphous form.

Physical Properties

Decomposition Point: 165° C.
$[\alpha]_D^{20} - 3.4°$ (C=1, in methanol).
Ultimate Analysis: $C_{24}H_{35}O_{14}N_3 \cdot 3H_2O$; Cald.: C; 44.79, H; 6.42, N; 6.53. Found: C; 45.23, H; 5.51, N; 6.38.
IR $\nu_{max}^{KBr}$ 1730 cm$^{-1}$ (COO Me).
$^1$H-NMR$_{400}^{ppm}$ $_{MHz}$ (D$_2$O, TSP) 1.413 (s, 3H), 1.605 (s, 3H), 2.061 (s, 3H), 3.807 (s, 3H).

EXAMPLE 6

Preparation of 5'-o-(4-N-acetyl-2,4-dideoxy-1-methoxycarbonyl-D-glycero-β-D-galacto-octapyranosyl) uridine 2 ml of a 90% trifluoroacetic acid solution containing 150 mg (0.273 millimol) of the compound produced in Example 5 was agitated at room temperature for 2 hours. After completion of the reaction, the solvent was distilled off and a small quantity of water was added thereto. The solution was then freeze-dried and dried in vacuo to obtain 150 mg of colorless amorphous mass which was subjected to silica gel column chromatography to be fractionated with chloroform: methanol=20:1, whereby 120 mg (Yield: 80%) of the captioned compound was obtained as a colorless amorphous mass.

The physical properties of the products are set forth below.

Decomposition Point: 158° C.
$[\alpha]_D^{20}$ 4.1° (C=1, in methanol).
Ultimate Analysis: $C_{21}H_{31}N_3O_{14} \cdot 2H_2O$; Cald.: C; 43.08, H; 6.07, N; 7.18. Found: C; 42.72, H; 5.26, N; 7.03.
$^1$H-NMR$_{400}^{ppm}$ $_{MHz}$ (D$_2$O, TSP) 1.83 (1H, 3-Hax), 2.06 (3H, —NHAc) 2.49 (1H, 3—Heq), 3.86 (3H, COOMe).

EXAMPLE 7

Preparation of 5'-o-(4-N-acetyl-2,4-dideoxy-3,6,7,8-tetra-o-acetyl-1-methoxycarbonyl-D-glycero-β-D-galacto-octapyranosyl uridine 1.5 ml of a 90% aqueous trifluoroacetic acid solution containing 50 mg (0.07 millimol) of the compound produced in Example 1 was agitated at room temperature for 2 hours. The solvent was distilled off, after the completion of the reaction, and a small quantity of water was then added to obtain a solution which was subjected to sequential freeze-dry and vacuum-dry steps, whereby 50 mg of the captioned compound was obtained as a colorless amorphous mass. The physical properties of the product are as follows.

Decomposition Point: 133° C.
IR $\nu_{max}^{KBr}$ 1735, 1680 cm$^{-1}$
$^1$H-NMR (D$_2$O) δH (DSS) 2.62 (1H, 3Heq), 3,85 (3H, COOMe)

REFERENCE EXAMPLE

This reference example shows the functions of the compounds of the invention for inhibiting metastasis of cancer cells.

Test Procedure

The cancer cells used in the test were the high metastasis factor species NL-17 and the low metastasis factor species NL-44, both originated from clone anenocarcinoma 26 of Balb/c Mouse. Details in this connection may be found by referring to Takashi Tsuruo et al., Cancer. Res., 43, 5437 (1983), and the article is incorporated herein as a reference.

Each of the cancer cells was cultivated in a carbon dioxide incubator for 24 hours in the presence of 0.1 mM of the compound obtained in EXAMPLE 3 (hereinafter referred to as compound [I]). The same family of mice were incubated with $5 \times 10^4$ cancer cells from their tail veins, and at the same time the mice were administered 0.25 mg or 0.5 mg of the compound [I]. After this, 0.25 mg or 0.5 mg of the compound [I] was administered intravenously at two times per a week. After 22 days from inoculation of cancer cells, the mice were killed and their lungs were enucleated. The thus enucleated lungs were weighed and the numbers of formed tuberosa were determined.

The results are shown in the following Table. As shown in the Table, the metastasis factors for metastasizing to the lungs of both of NL-17 and NL-44 were significantly inhibited by the pre-treatment and after-dosage of the compound [I] of the invention. It has been also found that the inhibition effects depended on the dosage amounts of the compound.

TABLE

| Function of Compound [I] in Experiments for Metastasis of NL-17 and NL-44 | | | | | | |
|---|---|---|---|---|---|---|
| Cancer Cell | Treatment | Number of Mice | Weight of Lung (mg) | Number of Metastasized Tuberosa | | |
| | | | | Large | Small | Total |
| — | — | 4 | 198 ± 12 | 0 | 0 | 0 |
| — | — | 4 | 407 ± 95 | 52 ± 16 | 28 ± 7 | 80 ± 22 |
| NL-17 | Compound [I]$^a$ | 4 | 318 ± 65 | 18 ± 7** | 14 ± 3** | 32 ± 9*** |
| — | — | 3 | 279 ± 18 | 19 ± 2 | 32 ± 4 | 51 ± 2 |
| NL-44 | Compound [I]$^a$ | 3 | 228 ± 10** | 16 ± 5 | 25 ± 4 | 40 ± 7 |
| — | — | 4 | 190 ± 16 | 0 | 0 | 0 |
| — | — | 4 | 370 ± 26 | 57 ± 13 | 31 ± 14 | 88 ± 23 |
| NL-17 | Compound [I]$^b$ | 4 | 243 ± 44*** | 13 ± 7*** | 13 ± 8* | 26 ± 14*** |
| — | — | 4 | 216 ± 12 | 19 ± 4 | 21 ± 5 | 40 ± 3 |
| NL-44 | Compound [I]$^b$ | 4 | 194 ± 9** | 5 ± 2*** | 14 ± 3* | 20 ± 4*** |

Cancer cell were treated before the inoculation with 0.1 mM of the compound for 24 hours. After inoculation, mice were dosed intravenously with 0.25$^a$ or 0.5$^b$ mg/mouse/3 days.
*P < 0.1,
**P < 0.5,
***P < 0.01
The treated groups are significantly differentiated from the untreated groups.

What is claimed is:

1. An N-acetylneuraminic acid represented by the general formula:

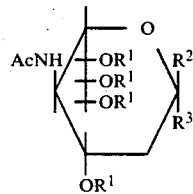

wherein the $R^1$ groups are, independently, hydrogen or acetyl; $R^2$ is selected from the group consisting of uridine, 5-fluoro-uridine, 2', 3'-isopropylidene-uridine and 5-fluoro-2',3-isopropylidene-uridine; and $R^3$ is carboxyl or methoxycarbonyl.

2. The N-acetylneuraminic acid derivative as claimed in claim 1, wherein $R^1$ is acetyl, $R^2$ is 2',3'-isopropylideneuridine and $R^3$ is methoxycarbonyl.

3. The N-acetylneuraminic acid derivative as claimed in claim 1, wherein $R^1$ is hydrogen, $R^2$ is 2',3'-isopropylideneuridine and $R^3$ is methoxycarbonyl.

4. The N-acetylneuraminic acid derivative as claimed in claim 1, wherein $R^1$ is hydrogen, $R^2$ is uridine and $R^3$ is carboxyl.

5. The N-acetylneuraminic acid derivative as claimed in claim 1, wherein $R^1$ is hydrogen, $R^2$ is 5-fluoro-2',3'-isopropylideneuridine and $R^3$ is methoxycarbonyl.

6. The N-acetylneuraminic acid derivative as claimed in claim 1, wherein $R^1$ is acetyl, $R^2$ is 5-fluoro-2',3'-isopropylideneuridine and $R^3$ is methoxycarbonyl.

7. The N-acetylneuraminic acid derivative as claimed in claim 1, wherein $R^1$ is hydrogen, $R^2$ is 5-fluorouridine and $R^3$ is methoxycarbonyl.

8. The N-acetylneuraminic acid derivative as claimed in claim 1, wherein $R^1$ is hydrogen $R^2$ is 5-fluorouridine and $R^3$ is carboxyl.

9. The N-acetylneuraminic acid derivative as claimed in claim 1, wherein $R^1$ is hydrogen, $R^2$ is uridine and $R^3$ is methoxycarbonyl.

10. The N-acetylneuraminic acid derivative as claimed in claim 1, wherein $R^1$ is acetyl, $R^2$ is uridine and $R^3$ is methoxycarbonyl.

11. A process for preparing an N-acetylneuraminic acid derivative represented by the following formula :

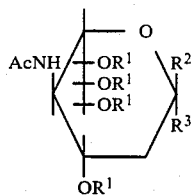

wherein the $R^1$ groups are independently, hydrogen or acetyl; $R^2$ is selected from the group consisting of uridine, 5-fluoro-uridine, 2,3-isopropylidene-uridine and 5-fluoro-2',3-isopropylideneuridine; and $R^3$ is carboxyl or methoxycarbonyl; which comprises reacting a compound represented by the general formula:

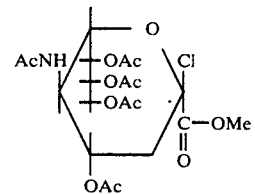

with a compound represented by the formula $R^2$-H [III], wherein $R^2$ is nucleoside residue, in the presence of a catalyst; to produce the reaction product represented by isolating and a formula [I] purifying the reaction product step through a dual-chromatography step.

12. The process as claimed in claim 11, wherein said isolation-purifying step is at least one of the dual-chromatography steps selected from the group consisting of:

adsorption chromatography/adsorption chromatography;

adsorption chromatography/partition chromatography;

partition chromatography/adsorption chromatography;

and partition chromatography/partition chromatography.

13. The process according to claim 12, wherein said adsorption and partition chromatography steps comprise using a column packed with a member selected from the group consisting of silica gel and alumina and elution is accomplished by one or more solvents selected from the group consisting of chloroform, methanol, ethyl acetate, ethanol, benzene, acetone and toluene.

14. The process as claimed in claim 11, wherein said compound represented by the formula [III] is a compound represented by the general formula:

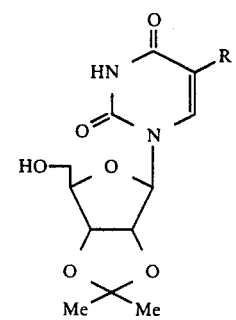

wherein R is hydrogen or fluorine, and Me is methyl.

15. The process as claimed in claim 11, wherein said reaction product is hydrolyzed before being subjected to said isolating and purifying step.

16. The process according to claim 15, wherein compound [II] is used in a ratio of at least about 1.2 moles per 1 mole of compound [III] in the step to produce said reaction product.

* * * * *